United States Patent [19]

Pappas

[11] 4,215,438
[45] Aug. 5, 1980

[54] PROSTHESIS FOR OSSICULAR CHAIN RECONSTRUCTION

[76] Inventor: Dennis G. Pappas, 2940 Clairmont, Ave., Birmingham, Ala. 35205

[21] Appl. No.: 5,215
[22] Filed: Jan. 22, 1979
[51] Int. Cl.³ .................. A61F 1/24; A61F 1/00
[52] U.S. Cl. ........................................ 3/1.9
[58] Field of Search ................... 3/1, 1.9, 1.91

[56] References Cited
U.S. PATENT DOCUMENTS

| | | | |
|---|---|---|---|
| 3,196,462 | 7/1965 | Robinson | 3/1 |
| 3,711,869 | 1/1973 | Shea, Jr. | 3/1 |
| 3,722,003 | 3/1973 | Walchle | 3/1 |

Primary Examiner—Ronald L. Frinks
Attorney, Agent, or Firm—Jennings, Carter & Thompson

[57] ABSTRACT

A prosthesis for reconstruction of the auditory ossicles. The prosthesis comprises essentially a goblet-shaped member, preferably of stainless steel or like inert material, the cup portion of which is disposed to receive the capitulum of the stapes while the stem portion is inserted into a hole drilled into the body of the incus. The prosthesis thus bridges the space between the stapes head and incus, the incus being repositioned against the malleus and the tympanic membrane.

1 Claim, 6 Drawing Figures

PROSTHESIS FOR OSSICULAR CHAIN RECONSTRUCTION

This invention relates to a prosthesis particularly adapted for the reconstruction of the auditory ossicles, and has for an object the provision of such a prosthesis which, when in place, will improve the conductive capability of the auditory chain.

In the art to which this invention relates, many prostheses have been used for reconstruction of the auditory ossicles. Such include wire and plastics. Autograph and homograph incuses and malleus heads, notched or molded, also have been employed One difficulty with plastic prostheses has been that they tend to extrude. The autograph and hemograph incuses and malleus heads, notched or molded, shift out of position. In both of the foregoing, although hearing results were often excellent shortly after the operation, longer follow-up frequently showed that hearing had gradually deteriorated. In addition to the above, bone chips and grafts have been used to bridge small gaps in the chain, but experience shows that in time these generally are absorbed.

As before stated, my invention comprises a goblet-shaped prosthesis comprising essentially a socket-like cup with a projectile stem. The cup end fits over the capitulum of the stapes and the stem is inserted into a hole drilled into the body of the incus, which has been repositioned. The goblet thus secures the ossicles in place, making a firm connection to the stapes capitulum, preventing healing migration and ankylosis of the repositioned incus on the middle ear mucosa or bone.

A prosthesis illustrating features of my invention is shown in the accompanying drawings forming a part of this application in which.

Figure 1:
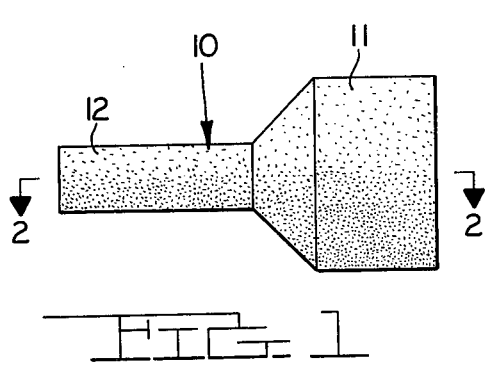
FIG. 1 is a greatly enlarged side elevational view of my improved prosthesis.
Figure 2:
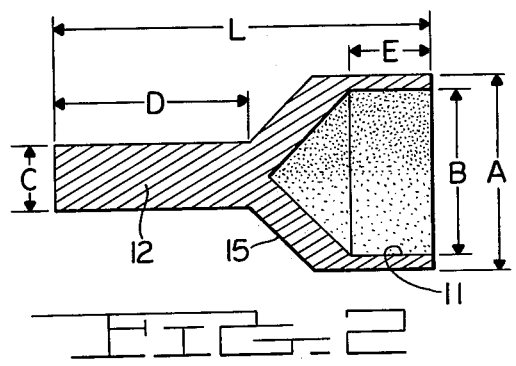
FIG. 2 is a detail sectional view taken generally along line 2—2 of FIG. 1.

Referring now to the drawings for a better understanding of my invention my improved prosthesis is indicated generally by the numeral 10. Thus, my invention may be described as being of generally goblet-like shape, there being on one end a cup-shaped opening 11 and on the opposite end a stem portion 12.

While dimensions may vary somewhat, I have found that the overall dimension L may be on the order of 0.098 inch; the outer diamter A of the cup part on the order of 0.054 inch; the inner diameter B of the cup being on the order of 0.047 inch; the diameter of the stem C on the order of 0.016 inch; the length D of the stem on the order of 0.045 inch, the depth of the cup portion E on the order of 0.034 inch. A conical section 15 about 0.019 inch long joins the stem and cup sections. As stated, the prosthesis preferably is made of stainless steel although there may be other materials which are suitable.

Figure 3:
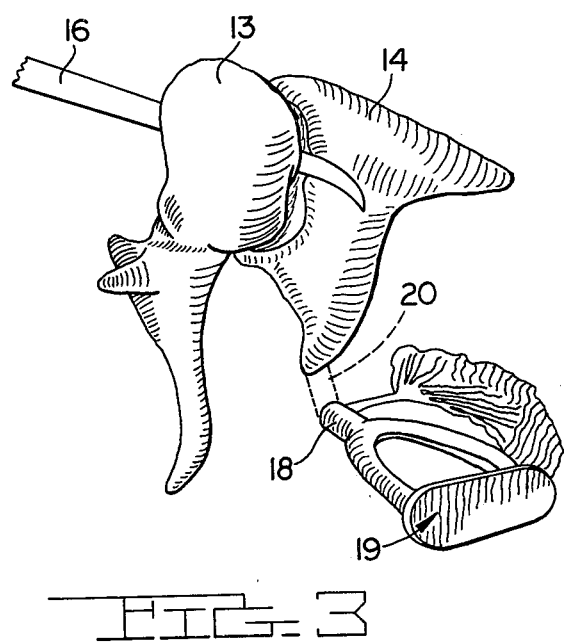
FIG. 3 is a view of principal parts of the ossicular chain showing the separation of the malleus from the incus and illustrating the deterioration of the capitulum of the incus.
Figure 4:
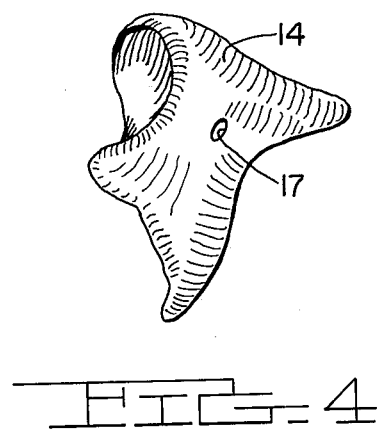
FIG. 4 is a detached view of the incus.

As is understood, the defect to be corrected is to repair the damage caused by the deterioration of the capitulum of the incus indicated by the dotted line 20, FIG. 3.

In carrying out the procedure, the malleus 13 is separated from the incus 14 by a suitable instrument 16. A hole to receive the stem portion 12 of the prosthesis is now drilled into the incus as illustrated at 17.

The prothesis is now fitted snugly over the capitulum 18 of the stapes 19.

Figure 6:
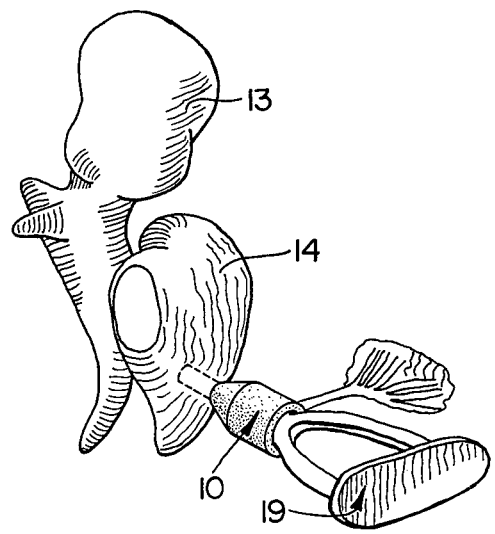
Figure 5:
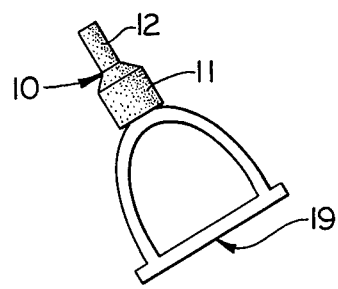
FIG. 5 is a view of the stapes with my improved prothesis in place on the capitulum thereof; and, FIG. 6 is a view of the ossicular chain showing my improved prosthesis in place, the chain being repositioned.

Having assembled the prosthesis onto the stapes the ossicular chain is now reassembled as shown in FIG. 6.

It will be noted that by the provision of the stem 12 which actually enters an opening formed in the incus, in combination with the cup portion which receives the capitulum of the stapes, I have provided a firm, effective and practical reconstruction of the chain.

In actual practice I have discovered that my invention is extremely practical and satisfactory. Furthermore, after observing about 150 patients who have been provided with my improved prosthesis, experience to date indicates that excellent results have been obtained in about 90% of this group. In this 90% group, closure of the air-borne gap has been zero to five decibels. Thus, the procedure employing my improved prosthesis results in the attainment of a high degree of accuity of hearing, approaching the degree of hearing possessed by a normal human ear.

While I have shown my invention in but one form, it will be obvious to those skilled in the art that it is not so limited but is susceptible of various changes and modifications without departing from the spirit thereof.

What I claim is:

1. In a prosthesis for reconstruction of the auditory ossicles,
    (a) a member of substantially rigid material having an open cup-like end and an integrally formed stem projecting axially from the closed end of the cup-like portion, said prothesis being approximately 0.098 inches in overall length, the cup-like portion having an outside diameter of approximately 0.054 and an inside diameter of approximately 0.047 inch, the cup-like portion being generally cylindrical shaped and about 0.034 inch long, said stem being approximately 0.016 inch in diameter and about 0.045 inch long, and
    (b) a conical section joining the cup and stem portions and being on the order of 0.019 inch long.

* * * * *